United States Patent
Rege et al.

(10) Patent No.: US 11,610,201 B2
(45) Date of Patent: Mar. 21, 2023

(54) TOKENIZED HEALTHCARE SERVICE PAYMENTS

(71) Applicant: Capital District Physicians Health Plan, Inc., Albany, NY (US)

(72) Inventors: Umesh Rege, Albany, NY (US); Brent Cooley, Albany, NY (US)

(73) Assignee: Capital District Physicians Health Plan, Inc., Albany, NY (US)

( * ) Notice: Subject to any disclaimer, the term of this patent is extended or adjusted under 35 U.S.C. 154(b) by 398 days.

(21) Appl. No.: 16/582,114

(22) Filed: Sep. 25, 2019

(65) Prior Publication Data

US 2021/0090081 A1   Mar. 25, 2021

(51) Int. Cl.
  *G06Q 20/40* (2012.01)
  *G16H 10/60* (2018.01)
  *G06Q 20/10* (2012.01)
  *G06Q 20/38* (2012.01)

(52) U.S. Cl.
  CPC .......... *G06Q 20/401* (2013.01); *G16H 10/60* (2018.01); *G06Q 20/102* (2013.01); *G06Q 20/3821* (2013.01)

(58) Field of Classification Search
  None
  See application file for complete search history.

(56) References Cited

U.S. PATENT DOCUMENTS

| | | | |
|---|---|---|---|
| 2010/0185466 A1* | 7/2010 | Paradis | G06Q 20/20 705/4 |
| 2015/0269559 A1* | 9/2015 | Inotay | G06Q 20/3274 705/44 |
| 2016/0321412 A1* | 11/2016 | Basri | G16H 10/60 |

(Continued)

FOREIGN PATENT DOCUMENTS

WO   WO-2017218138 A1 * 12/2017 ............. G06Q 20/28

OTHER PUBLICATIONS

Zainab Alhadhrami et al., Introducing blockchains for Healthcare, 2017 International Conference on Electrical and Computing Technologies and Applications (ICECTA) (2017), https://ieeexplore.ieee.org/stamp/stamp.jsp?tp=& arnumber=8252043 (last visited on Nov. 3, 2022) (Year: 2017).*

*Primary Examiner* — John P Go
*Assistant Examiner* — Nicholas Akogyeram, II
(74) *Attorney, Agent, or Firm* — Loeb & Loeb LLP

(57) ABSTRACT

A computer-implemented method for expediting processing of a payment for a patient's healthcare service with a healthcare provider includes displaying an out-of-pocket cost for a patient for a healthcare service at a display interface of a computer device prior to the healthcare service being rendered. After patient selection of the healthcare service and payment of any out-of-pocket costs, a health token is issued to the patient as cryptocurrency for payment of the healthcare service. The health token is received from the healthcare provider after the healthcare provider renders the healthcare service, receives the health token from the patient for payment of the healthcare service, and embeds data pertaining to the healthcare service into the health token. Based on the data embedded in the health token, the healthcare service is approved or disapproved. If the healthcare service is approved, a payment for the healthcare service is issued to the healthcare provider.

17 Claims, 10 Drawing Sheets

(56) References Cited

U.S. PATENT DOCUMENTS

| | | | | |
|---|---|---|---|---|
| 2017/0364914 A1* | 12/2017 | Howard | ............... | G06Q 20/405 |
| 2018/0039744 A1* | 2/2018 | Nusbaum | ........... | G06Q 30/0641 |
| 2018/0117447 A1* | 5/2018 | Tran | ...................... | G16H 10/60 |
| 2018/0247063 A1* | 8/2018 | Li | ......................... | H04L 63/062 |
| 2019/0228473 A1* | 7/2019 | Tabbaa | .................. | G16H 15/00 |
| 2019/0266597 A1* | 8/2019 | Mohtar | ................ | G06Q 20/065 |
| 2019/0363870 A1* | 11/2019 | Wagner | ............... | G06Q 20/401 |

* cited by examiner

FIG. 9

TOKENIZED HEALTHCARE SERVICE PAYMENTS

TECHNICAL FIELD

Embodiments discussed herein generally relate to a blockchain-backed health token system for accelerating healthcare service payments to healthcare providers, and for providing friction-less financial experience to patients and healthcare providers.

BACKGROUND

Healthcare administrative overhead costs may account for a significant portion of healthcare spending. At least part of these overhead costs may be due to the antiquated claims-based retrospective insurance payment model that frequently results in unexpected and/or delayed bills to patients after a healthcare service.

In a traditional claims-based insurance model, a healthcare provider submits a claim on behalf of a patient to an insurance payer (e.g., a health insurance company) after providing the patient with a healthcare service. After the claim is checked for errors, and after any errors are resolved, the claim goes through an adjudication process to determine the amount to pay the provider for the healthcare service. In some select circumstances, patient clinical encounter data may be shared between the healthcare provider and the healthcare payer in the process of finalizing the payment amount to the healthcare provider. Once the healthcare provider receives payment from the payer, the healthcare provider may submit a bill to the patient for any remaining balance for the healthcare service. As many patients, such as those with a high deductible-based insurance plan, may not know their share of the costs until after claim adjudication and billing. They may be unprepared to meet their payment obligations in a timely manner. A delinquent patient account may require the healthcare provider to send additional statements to the patient to collect unpaid balances. If the bill remains unpaid, the healthcare provider may turn the bill over to a debt collector. Consequently, revenue flow to healthcare providers may be slow, sometimes with months passing before full payments are received for a healthcare service.

U.S. Pat. No. 10,340,038 describes a healthcare validation system, whereby peers in a healthcare network manage a healthcare historical blockchain associated with stakeholder, such as a patient. The healthcare historical blockchain represents a chronicle or ledger of the stakeholder's validated healthcare transactions, such as birth, doctor visits, and surgeries.

However, there is a need for improved payment processing systems that provide more timely revenue flow to healthcare providers for healthcare services, and reduce administrative expenses involved in payment or debt collection. Though accelerated payments is one of the goals, another important objective is to provide full cost (and bill) transparency to members and provide friction-less financial experience to patients and healthcare providers. Additionally, there is a need for systems that improve the transparency of a patient's cost share for a healthcare service in advance of the healthcare service. Further, there is a need for systems that facilitate the sharing of clinical encounter data and other data between healthcare providers and healthcare payers. The embodiments of the present disclosure attempt to provide a technical solution to address these needs.

SUMMARY

Embodiments disclosed herein apply a blockchain technology-backed health token system to provide a technical solution to the above challenges. In one embodiment, a computer-implemented method for expediting processing of a payment for a patient's healthcare service with a healthcare provider includes displaying an exact out-of-pocket cost for the patient for the healthcare service at a display interface associated with a computer device of the patient, prior to the healthcare service being rendered. The method further includes issuing the patient a health token as cryptocurrency for future payment of the healthcare service with the healthcare provider. The health token may be stored in a digital wallet on the computer device of the patient. The method further includes receiving the health token from the healthcare provider after the healthcare provider renders the healthcare service, receives the health token from the patient for payment of the healthcare service, and embeds data pertaining to the healthcare service into the health token. Additionally, the method further includes determining if the healthcare service is approved based at least on the data embedded in the health token, and issuing a full payment to the healthcare provider for the healthcare service if the healthcare service is approved.

In another embodiment, a health token system for expediting processing of a payment for a patient's healthcare service with a healthcare provider includes a blockchain network including at least a payer computer device associated with a payer, a provider computer device associated with a healthcare provider, and a patient computer device associated with the patient. The health token system further includes a patient interface module associated with the payer computer device configured to issue the patient a health token as cryptocurrency for payment of the healthcare service prior to the healthcare service being rendered. The health token may be stored in a digital wallet on the patient's computer device. The health token system further includes a provider interface module associated with the payer computer device configured to receive the health token from the provider computer device after the healthcare provider renders the healthcare service and receives the health token from the patient for payment of the healthcare service. Additionally, the health token system further includes an approval module associated with the payer computer device configured to approve the healthcare service and approve issuance of a full payment to the healthcare provider for the healthcare service.

BRIEF DESCRIPTION OF THE DRAWINGS

The disclosure may be better understood by reference to the detailed description when considered in connection with the accompanying drawings. The components in the figures are not necessarily to scale, emphasis instead being placed upon illustrating the principles of the disclosure.

FIG. 9 is an exemplary display interface of the provider computer device, according to one embodiment.

DETAILED DESCRIPTION

Figure 1:
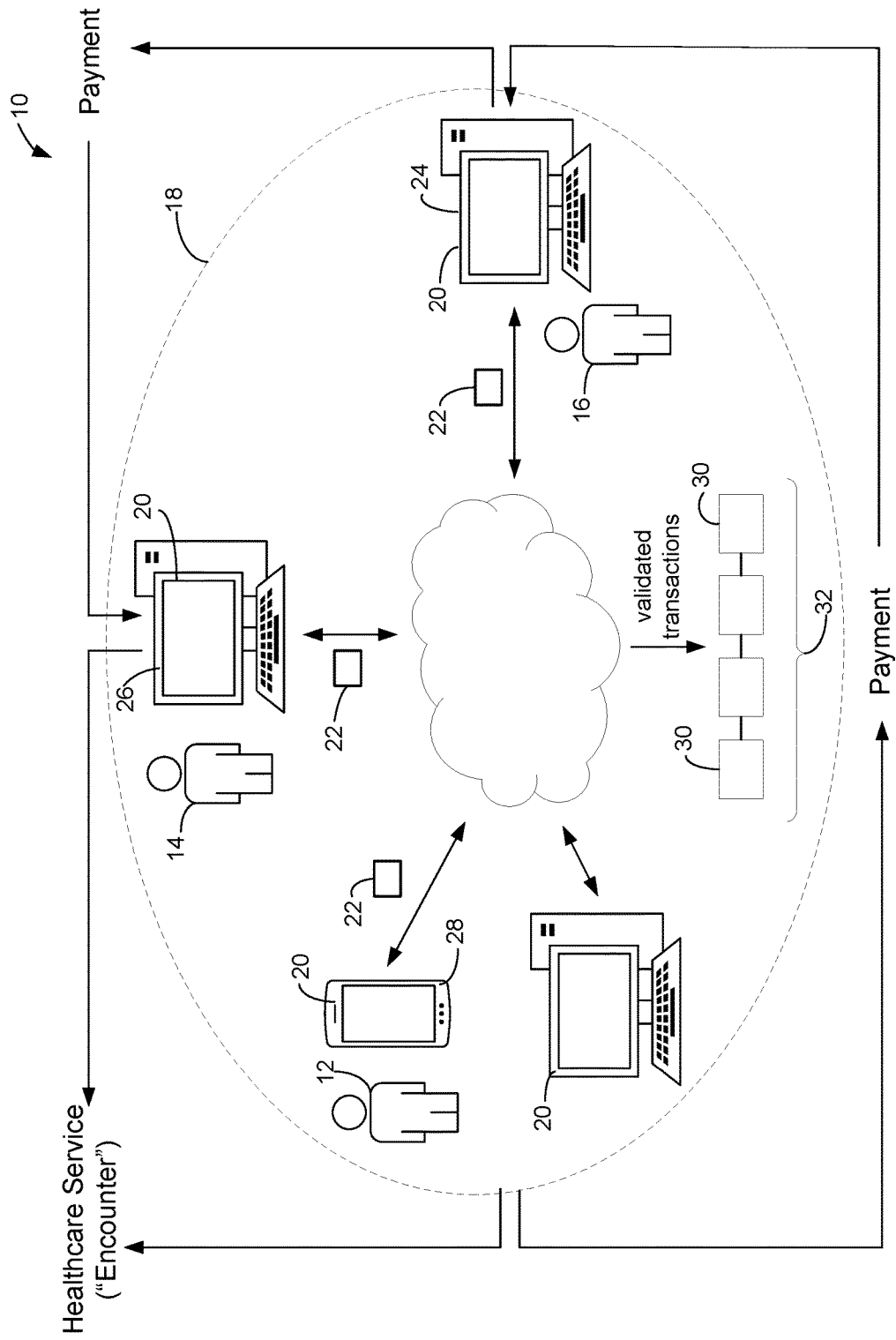
FIG. 1 is a schematic representation of a health token system for accelerating processing of healthcare service payments, according to one embodiment.

Referring now to the drawings and with specific reference to FIG. 1, a health token system 10 is shown. The health token system 10 may facilitate exchanges of payments and data between a patient 12, a healthcare provider 14, and a payer 16. As explained below, the health token system 10 may expedite processing of a payment to the healthcare provider 14 after the healthcare provider 14 provides a healthcare service to the patient 12. In the present disclosure, the healthcare service may alternatively be referred to as an "encounter" between the healthcare provider 14 and the patient 12. As used herein, the payer 16 may be a sponsor or a health insurer with which the patient has a healthcare plan. The healthcare provider 14 may be any person or entity capable of delivering a healthcare service such as, but not limited to, a doctor, a nurse, a doctor's office, a hospital, a hospice care provider, a nursing home, a physician's assistant, a physical therapist, an alternative medicine practitioner, an optometrist, an ophthalmologist, a dentist, an orthodontist, other types of healthcare practitioners, or a group or team of any of the foregoing.

The health token system 10 may include a blockchain network 18, or a peer-to-peer decentralized network of peer computer devices 20 (or nodes) over which the patient 12, the healthcare provider 14, and the payer 16 exchange health tokens 22 for healthcare services that the patient 12 has received or plans to receive from the healthcare provider 14. The blockchain network 18 may at least include a payer computer device 24 associated with the payer 16, a provider computer device 26 associated with the healthcare provider 14, a patient computer device 28 (e.g., a smartphone, tablet, or a personal computer) associated with the patient 12, as well as any additional peer computer devices 20 in the blockchain network 18. Transactions between the patient 12, the healthcare provider 14, and the payer 16 using the health tokens 22 may be validated within the blockchain network 18 by the peer computer devices 20 using a consensus program, and added as blocks 30 to a blockchain 32. As is understood by those skilled in the art, the blockchain 32 is a ledger of transactions that is distributed on the blockchain network 18.

For a specific healthcare service or encounter, a health token 22 may be exchanged between the peer computer devices 20 via the internet, LAN, WAN, VPN, or other types of networks. The health token 22 may be a form of cryptocurrency that includes funds from one or both of the patient 12 and the payer 16 for payment of the healthcare service. In addition, the health token 22 may define rules that must be satisfied for the transfer of payment from the payer 16 to the healthcare provider 14 for the healthcare service. The rules embedded in the health token 22 may be rules to ensure that the healthcare provider 14 is valid, the encounter is of the agreed type of encounter, and that proper clinical data is captured during the encounter. As non-limiting examples, the rules may include rules or criteria for validating the healthcare provider's 14 credentials, approved specialties, and place of service, as well as rules or criteria defining the type of clinical encounter data and other data that the payer 16 requires from the healthcare provider 14 to approve payment. The health token 22 may also serve as a vehicle for direct transfer of the clinical encounter data and other data from the healthcare provider 14 to the payer 16. Additionally, the health token 22 may have agreements embedded thereon, such as multiparty agreements between the payer 16, the patient 12, and the healthcare provider 14. For instance, the health token 22 may have agreed upon cost values for the healthcare service embedded thereon, such that all parties (including the patient 12, the healthcare provider 14, and the payer 16) know the exact pricing for the healthcare service before it is performed.

Figure 2:
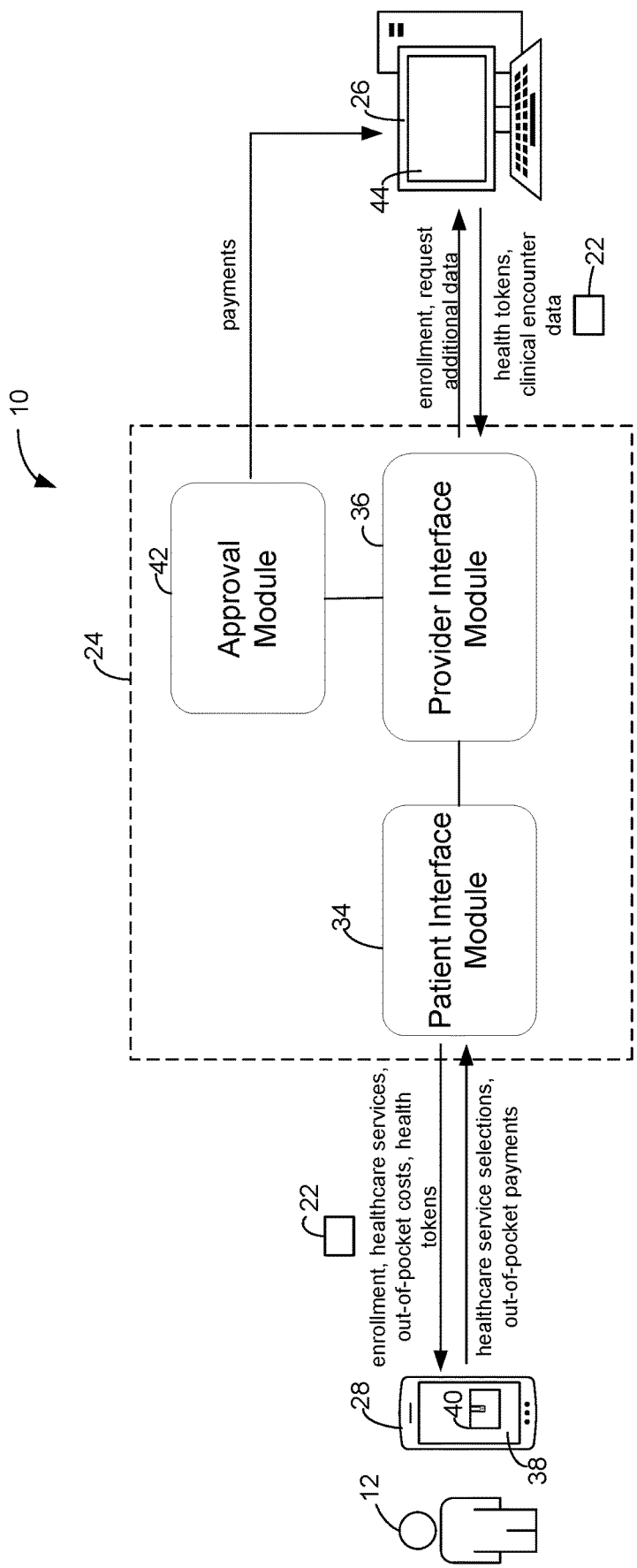
FIG. 2 is a schematic representation of exchanges between a payer computer device, a provider computer device, and a patient's computer device within the health token system, according to one embodiment.

Turning to FIG. 2, the payer computer device 24 may include a health token application downloaded thereon that includes a patient interface module 34 that interfaces with the patient's computer device 28, and a provider interface module 36 that interfaces with the provider computer device 26. The patient interface module 34 may be configured to interface with the health token application downloaded on the patient's computer device 28 and provide content for the patient 12 to view and select at a display interface 38 of the computer device 28. The patient interface module 34 may provide a list of healthcare services for selection by the patient 12, as well as the exact out-of-pocket costs (if any) that the patient 12 must pay for each of the healthcare services. Additionally, the patient interface module 34 may receive patient requests or selections for future healthcare services, receive out-of-pocket payments for selected healthcare services, and issue health tokens 22 for the selected healthcare services. The health token application may allow the patient 12 to view the healthcare services, select desired future healthcare services, pay any out-of-pocket costs for the selected healthcare services, and obtain the health tokens 22 for the selected healthcare services at the display interface 38. The obtained health tokens 22 may be stored in a digital wallet 40 on the patient's computer device 28 until retrieved by the patient 12 for payment after completion of the selected healthcare services.

The provider interface module 36 may be configured to interface with the health token application downloaded on the provider computer device 26. Through the health token application, the provider interface module 36 may receive health tokens 22 from the provider computer device 26 after the associated healthcare services are rendered and the healthcare provider collects the health tokens 22 from the patient 12. The health tokens 22 received from the provider computer device 26 may have clinical encounter data and other data pertaining to the associated healthcare services embedded thereon. The health token application may serve as a medium through which the healthcare provider 14 may scan health tokens 22 from the patient 12 after the completion of healthcare services, store the scanned health tokens 22, embed required clinical encounter data and other data pertaining to the completed healthcare services into the associated health tokens 22, and submit the health tokens 22 to the payer computer device 24 for redemption.

The provider interface module 36 may be associated with, or may include, an approval module 42 that approves the healthcare services for which the health tokens 22 are submitted based on the clinical encounter data and other data embedded in the health tokens 22. Specifically, the approval module 42 may determine whether the clinical encounter data and other data embedded in each health token 22 meets the pre-defined approval rules embedded in the health token 22. The approval module 42 may be within the payer's network. When the patient 12 submits a health token 22, the provider computer device 26 may check the validity of the health token 22 through interface with the approval module 42. In other arrangements, the health token 22 may have all the rules necessary to conduct validation/approval, perhaps separate from the payer. If the healthcare service is approved, the approval module 42 may approve issuance of an electronic payment to the provider computer device 26, or may otherwise approve direct payment (e.g., via check, etc.) to the health care provider 14. If the healthcare service is not approved, the provider interface module 36 may send a request for additional clinical encounter data or other data to the provider computer device 26 as necessary to satisfy the approval rules within the health token 22. The request for additional data may be viewed at a display interface 44 of the provider computer device 26 through the health token application. In response, the healthcare provider 14 may embed the requested additional data into the health token 22, and resubmit the health token 22 for redemption until the healthcare service is approved by the approval module 42. It will be understood that the modules of the payer computer device 24 as described above are merely exemplary, and that the functions of the payer computer device 24 in the health token system 10 may be performed by a single module or processing unit, or the functions may be distributed over multiple modules in different ways than described above.

Figure 3:
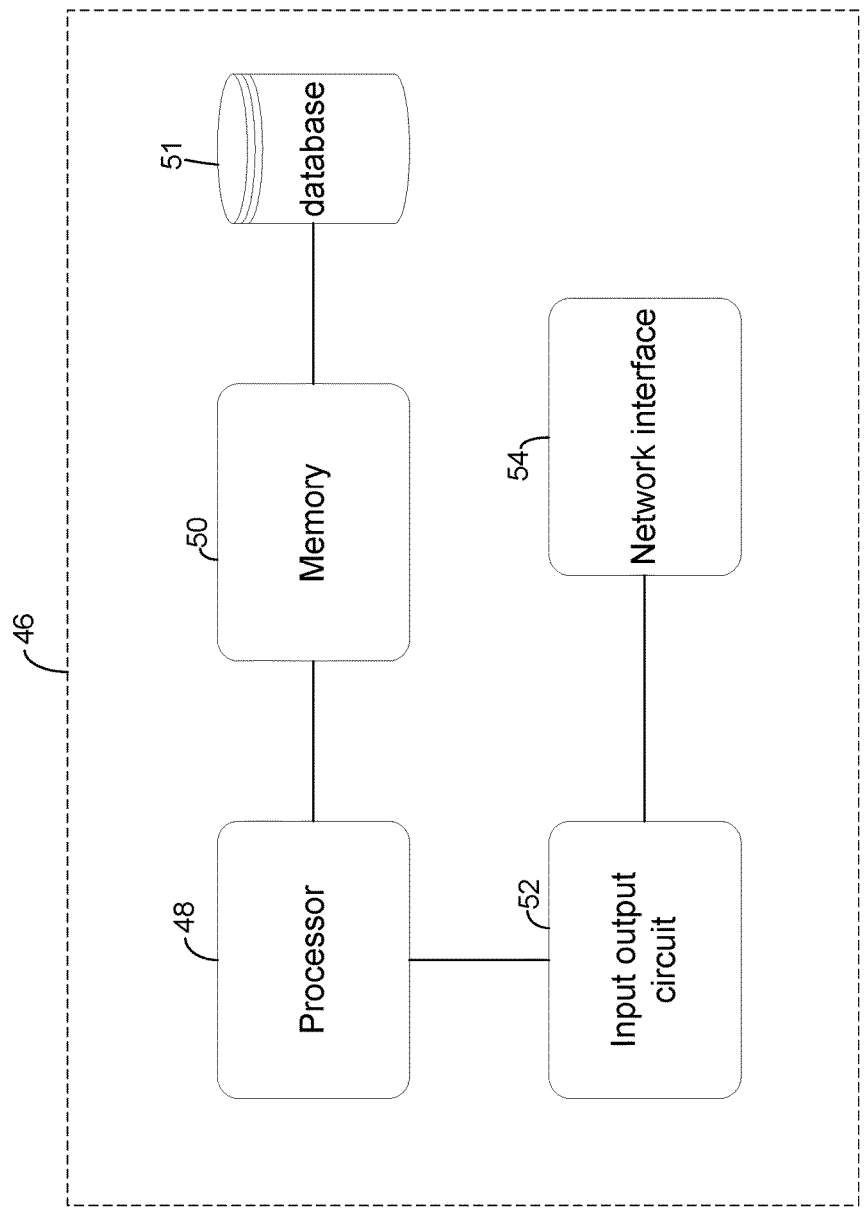
FIG. 3 is a schematic representation of a computer configured to perform at least some of the functions of the system of FIGS. 1 and 2, according to one embodiment.

A computer device 46 configured to perform at least some of the functions of the health token system 10 is shown in FIG. 3. The computer device 46 may be representative of any one of the payer computer device 24, the provider computer device 26, and the patient computer device 28. The computer device 46 may include one or more processors 48 configured according to computer executable instructions for carrying out at least some of the above-described functions of the payer computer device 24, the provider computer device 26, or the patient computer device 28. The functions may be implemented as software code or computer readable instructions that are executed by the processor 48. The computer device 46 may further include a memory 50 configured to store computer executable instructions and assist the processor 48. A database 51 may be associated with the memory 50 and may store data, such as data pertaining to the blockchain 32. In addition, an input output circuit 52 may be in communication with the processor 48, and may be involved in receiving inputs and providing outputs. The computer device 46 may further include a network interface 54 to enable communication with the peer communication devices 20 over the blockchain network 32.

Figure 4:
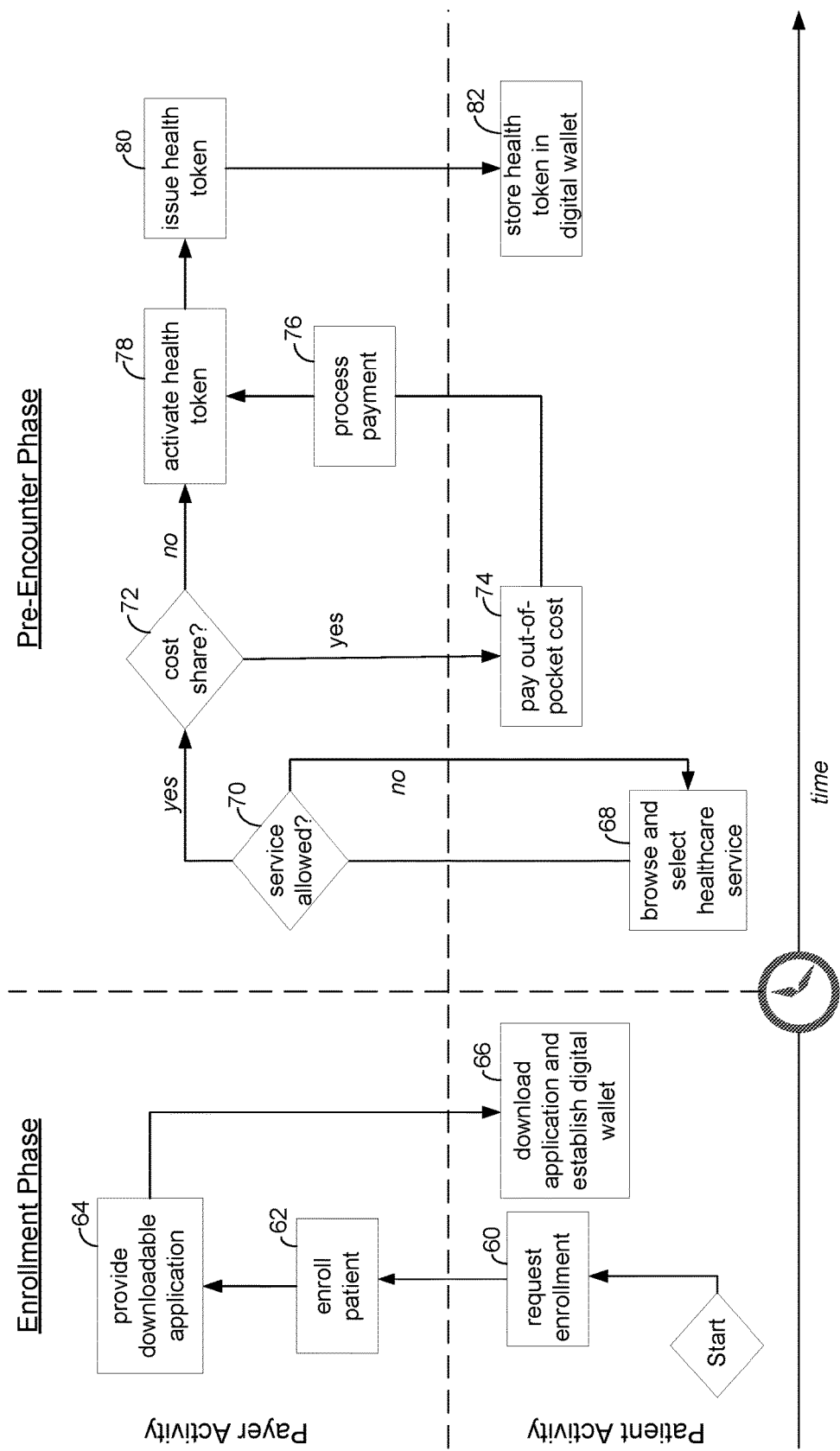
FIG. 4 is a flowchart illustrating a computer-implemented method for enrolling the patient in the health token system, and for issuing the patient a health token for a healthcare service during a pre-encounter phase, according to one embodiment.

Referring to FIG. 4, an exemplary method for enrolling the patient 12 in the health token system 10, and for issuing the patient 12 a health token 22 for a healthcare service is shown. The enrollment may occur during an "enrollment phase", and the issuing of the health token 22 may occur during a "pre-encounter phase" prior to the healthcare service being performed. The steps shown in FIG. 4 are separated according to activities performed by the patient 12 ("patient activity") using the patient computer device 28, and activities performed by the payer 16 ("payer activities") using the payer computer device 24. During the initial enrollment phase, the patient 12 may request enrollment in the health token system 10 at a block 60. For example, the patient 12 may submit an enrollment request on an internet website hosted by the payer 16. If the patient 12 qualifies for enrollment, the payer 16 may enroll the patient 12 in the health token system 10, and provide the patient 12 with the downloadable health token application according to the blocks 62 and 64. The patient enrollment process may involve providing the patient 12 with an identifier, such as a unique address or other identifier, for the patient 12 within the health token system 10. If the payer 16 is the patient's health insurer, the enrollment process may also involve enrolling the patient in the payer's health insurance plan if the patient is not already enrolled, and associating the patient's identifier with the patient's health insurance identification number, such as an insurance member ID number. According to a next block 66, the patient 12 may download the health token application on the computer device 28. The health token application may establish the digital wallet 40 unique to the patient 12 on the patient's computer device 28. The block 66 may complete the enrollment phase.

During the pre-encounter phase, the patient 12 may browse and select a future healthcare service at the display interface 38 using the downloaded health token application (block 68). If the payer 16 is the patient's health insurer, the healthcare services displayed to the patient 12 may be healthcare services that are at least partially covered by the patient's healthcare plan. In other arrangements, the healthcare services displayed to the patient 12 may also include healthcare services that are not covered by the patient's healthcare plan. At a next block 70, the payer computer device 24 may determine whether the patient's selected service is allowed, such as by referencing the patient's healthcare plan and determining whether the patient qualifies for the benefit. If the payer computer device 24 determines that the service is not allowed, the patient 12 may receive a notification, and the method may revert to the block 68 until the patient selects a healthcare service that is allowed.

If the payer computer device 24 determines that the service is allowed, the payer computer device 24 may determine if there is any cost share between the payer 16 and the patient 12 for the selected healthcare service (block 72). For example, the cost share may be determined by referencing the patient's healthcare plan and benefits, including any deductible, copay, or coinsurance information. If the healthcare service does include a cost share, the payer computer device 26 may provide the exact out-of-pocket cost to the patient 12, and allow the patient to submit a payment to cover the exact out-of-pocket cost (block 74). If the payment is successfully processed (block 76), the payer computer device 24 may activate the health token 22 (block 78) and issue the health token 22 to the patient 12 (block 80). The issued health token 22 may then be stored in the patient's digital wallet 40 for future use at the healthcare provider 14 (block 82). If, however, the selected healthcare service does not include a cost share, then the payer computer device 24 may directly activate and issue the health token 22 to the patient 12 (blocks 78 and 80), without requiring a payment from the patient 12.

Figure 5:
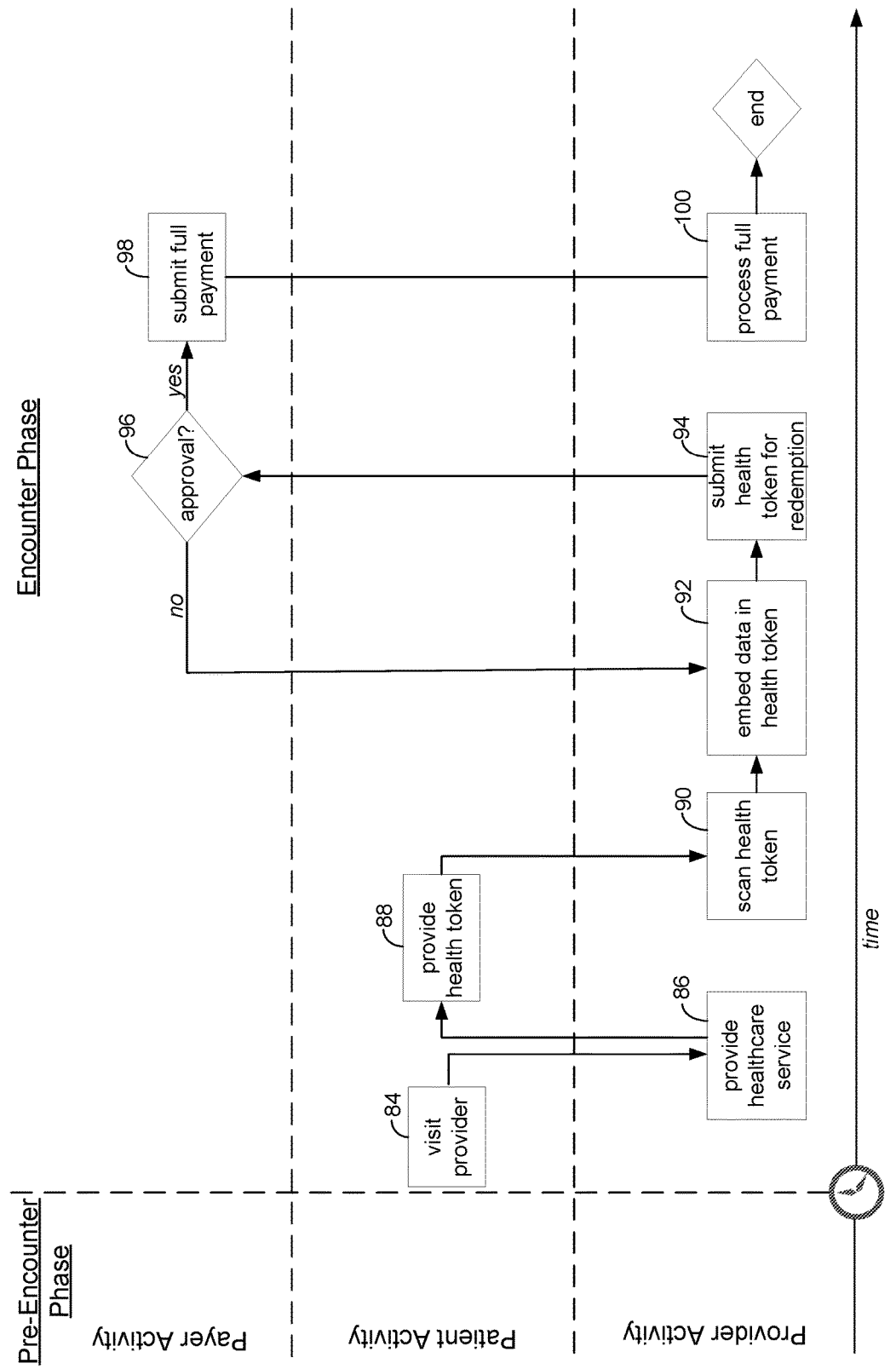
FIG. 5 is a flowchart illustrating a computer-implemented method for processing the health token during an encounter phase, according to one embodiment.

A method for processing the issued health token 22 during the encounter phase is shown in FIG. 5. The steps shown in FIG. 5 are separated according to steps performed by the patient 12 ("patient activity"), the healthcare provider 14 ("provider activity"), and the payer 16 ("payer activity"), with at least some of the steps being performed using the patient computer device 28, the provider computer device 26, and the payer computer device 24, respectively. At blocks 84 and 86, the patient 12 may visit the healthcare provider 14, and the healthcare provider 14 may provide the selected healthcare service. Following completion of the service, the patient 12 may retrieve the health token 22 stored in the digital wallet 40, and provide the health token 22 to the healthcare provider 14 (block 88). The healthcare provider 14 may use the health token application to scan the health token 22 at the provider computer device 26 and retrieve token details and rules embedded therein (block 90). Additionally, the healthcare provider 14 may utilize the health token application to embed any clinical encounter data or other data into the health token 22 as specified by the rules in the health token 22 (block 92). As non-limiting examples, the data may include healthcare provider credentials, approved specialties, place of service, clinical encounter data, lab test results, evaluations, prescriptions, and any diagnoses made during the healthcare service.

The healthcare provider 14 may subsequently submit the health token 22 with the embedded data to the payer 16 for redemption according to a block 94. Upon receipt of the submitted health token 22, the payer computer device 16 may determine whether the healthcare service is approved based at least on the data embedded in the health token 22 (block 96). More specifically, the payer computer device 24 may determine whether the data embedded in the health token 22 satisfies the approval rules specified by the health token 22. If the embedded data does not satisfy the rules, then the payer computer device 16 may request additional data from the healthcare provider 14, and the healthcare provider 14 may respond by embedding the requested additional data into the health token 22 (block 92) and resubmitting the health token 22 to the payer 16 for redemption (block 94). Once the rules on the token 22 are satisfied and the healthcare service is approved, the payer 16 may submit the payment to the healthcare provider 14 for the healthcare service using fiat currency (block 98). As the patient 12 has already met his or her cost share obligations prior to the healthcare service, the payment to the healthcare provider 14 may be made in full. As used herein, a full payment is a payment that includes the exact pricing for the healthcare service, as agreed upon by the healthcare provider and the payer prior to the healthcare service being rendered. The healthcare provider 14 may then process the payment at block 100.

In view of the methods of FIGS. 4-5, it can be seen that traditional post-service claim adjudication is eliminated with the health token system 10 as patient benefits, cost share, and service pricing are determined and established at the time of health token provisioning, prior to the healthcare service being performed. Furthermore, the patient 12 fulfills his or her cost share obligations prior to visiting the healthcare provider 14 for the healthcare service. The health token 12 also serves to facilitate exchange of data between the payer 16 and the healthcare provider 14, thereby improving the efficiency of the payer's approval process. Accordingly, the health token system 10 reduces the time between the healthcare service and the healthcare payment to the healthcare provider 14, and ensures that the healthcare provider 14 is paid the exact and agreed-upon amount for the service. This results in a faster revenue cycle, and reduces or eliminates patient debt as well as the healthcare provider's overhead and expense associated with debt collection.

Figure 6:
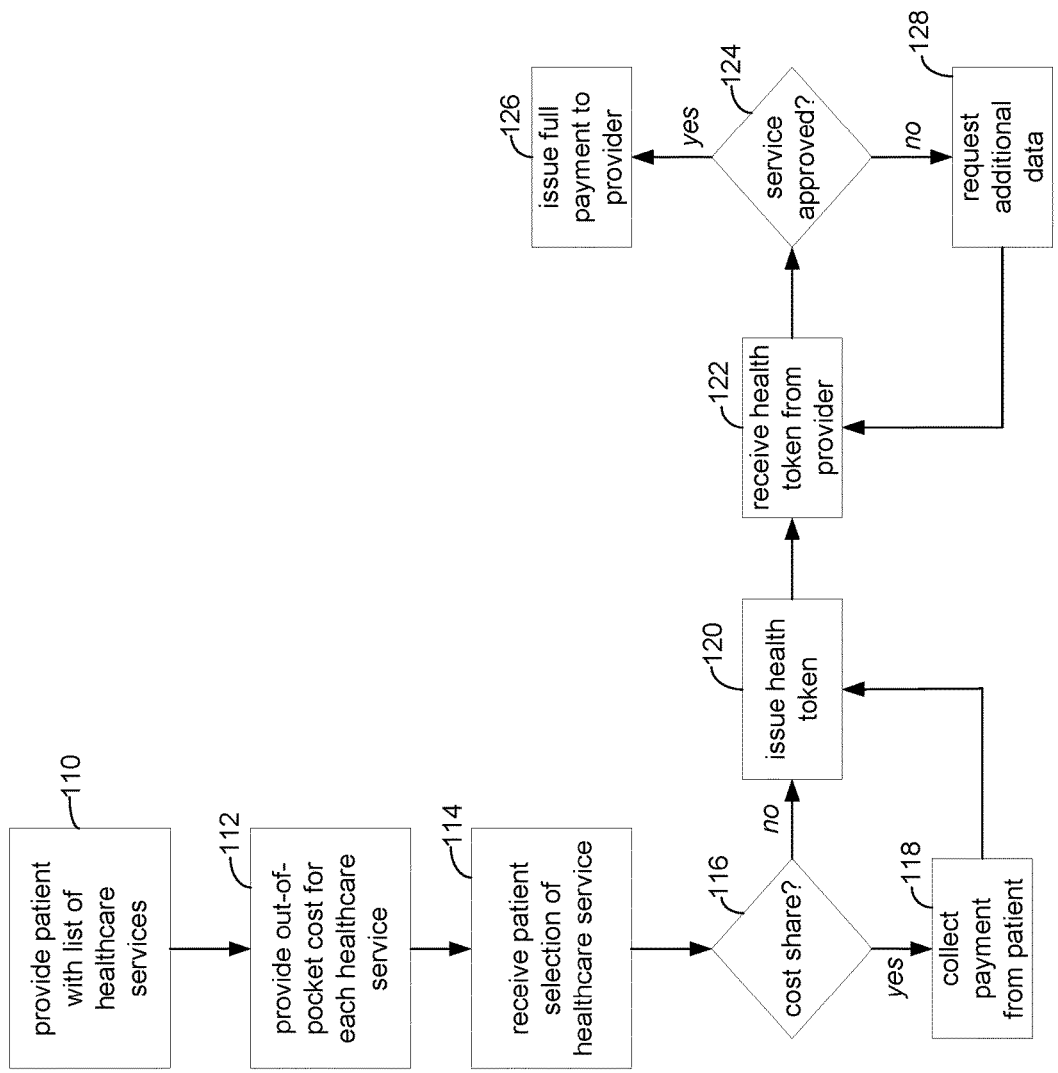
FIG. 6 is a flowchart illustrating a computer-implemented method for processing the payment for the healthcare service using the health token system as performed at the payer computer device, according to one embodiment.

Turning to FIG. 6, a method for processing a payment for a healthcare service as performed by the payer 16 using the payer computer device 24 is shown. The payer computer device 24 may interface with the patient's computer device 28 and the provider computer device 26 via the health token application to perform at least some of the steps shown in FIG. 6. At blocks 110 and 112, the payer 16 may provide the patient 12 with a list of healthcare services and any out-of-pocket costs for each of listed healthcare services for viewing at the patient's display interface 38. At a next block 114, the payer 16 may receive the patient's selection or request for a future healthcare service as the user selects a desired healthcare service from the list at the display interface 38. At a block 116, the payer computer device 16 may determine if there is a cost share between the payer 16 and the patient 12 for the selected healthcare service. If there is a cost share, the payer 16 may collect a payment from the patient 12 to cover the patient's out-of-pocket cost (block 118). Payment may be made electronically by the patient 12 via the health token application by means such as a credit card. Once payment from the patient is received and successfully processed, the payer 16 may issue a health token 22 to the patient 12 for the selected healthcare service (block 120). If there is no patient out-of-pocket cost associated with the selected healthcare service, then the payer 16 may issue the health token 22 without collection of a payment from the patient 12.

At a next block 122, the payer 16 may receive the health token 22 from the healthcare provider 14 after the healthcare provider 14 renders the healthcare service, receives and scans the health token 22 from the patient 12, and embeds clinical encounter data and/or other data as prescribed by the rules in the health token 22. The payer 16 may determine whether the healthcare service is approved at least based on the data and rules embedded in the health token 22 (block 124). If the embedded data meets the criteria defined by the health token 22 for approval, then the payer 16 may approve the healthcare service and issue a full payment to the healthcare provider 14 (block 126). If the embedded data does not meet the criteria for approval, then the payer 16 may request additional data from the healthcare provider 14 (block 128) until the embedded data meets the approval criteria and the healthcare service is approved.

Figure 8:
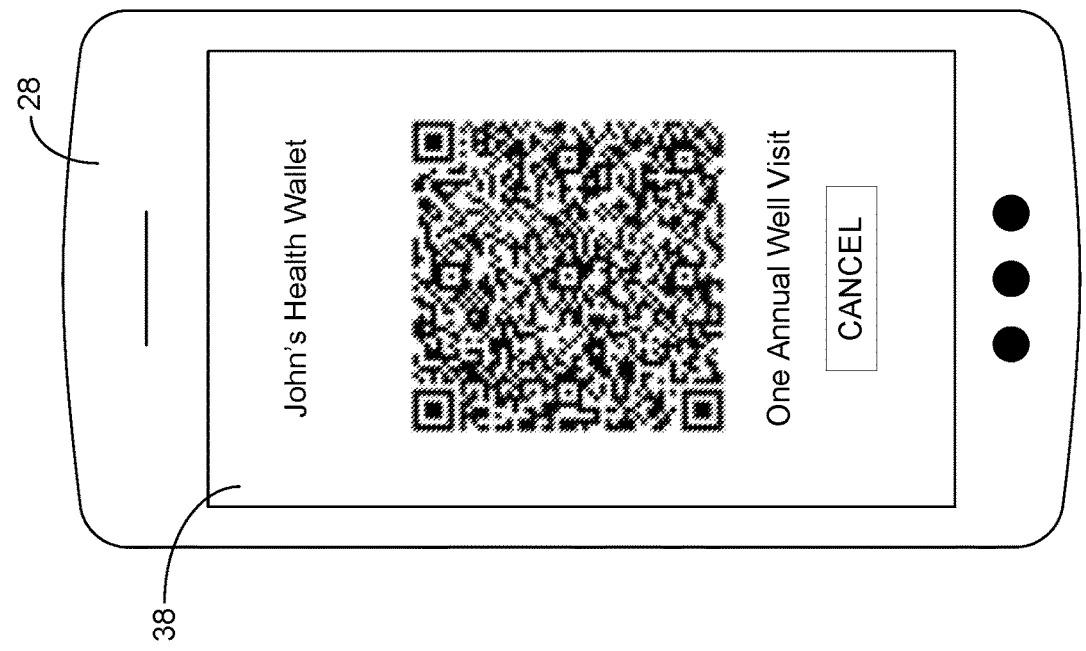
FIG. 8 is another exemplary display interface of the patient's computer device, according to one embodiment.
Figure 7:
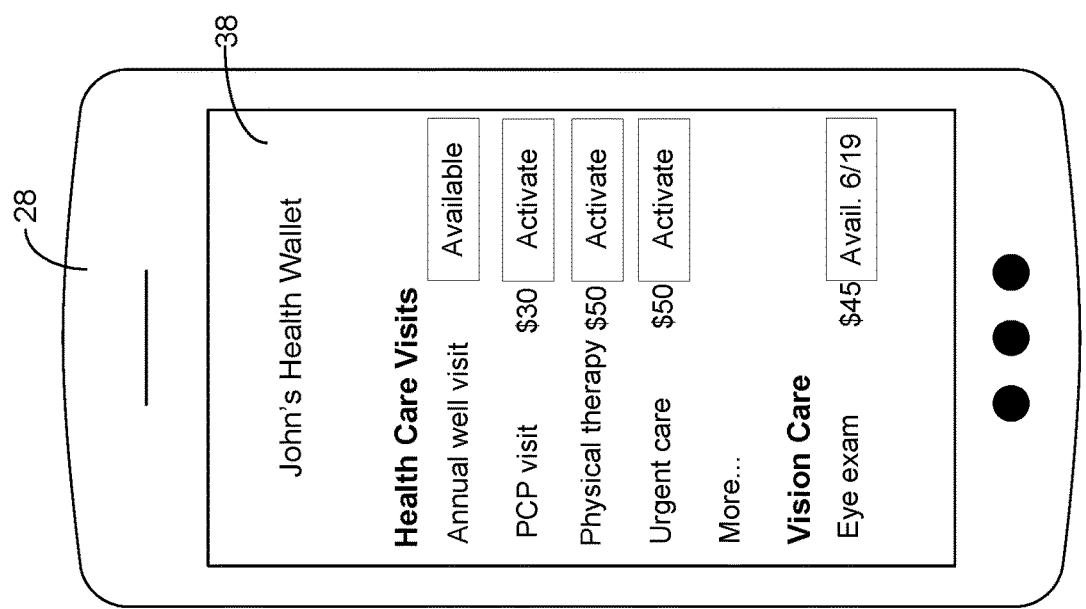
FIG. 7 is an exemplary display interface of the patient's computer device, according to one embodiment.

FIGS. 7 and 8 show exemplary display interfaces 38 of the patient's computer device 28 when using the health token application. Referring to FIG. 7, the patient 12 may view the list of healthcare services and any associated out-of-pocket costs for each of the healthcare services. The patient 12 may also select a desired healthcare service by selecting "activate", which will either prompt the patient 12 to submit a payment for the out-of-pocket cost and subsequently activate and issue a health token 22 for the selected healthcare service, or activate and issue the health token 22 directly if the patient does not have an out-of-pocket cost for the service. FIG. 8 shows an exemplary digital wallet 40 with an activated health token 22 for a future planned healthcare service.

Figure 9:
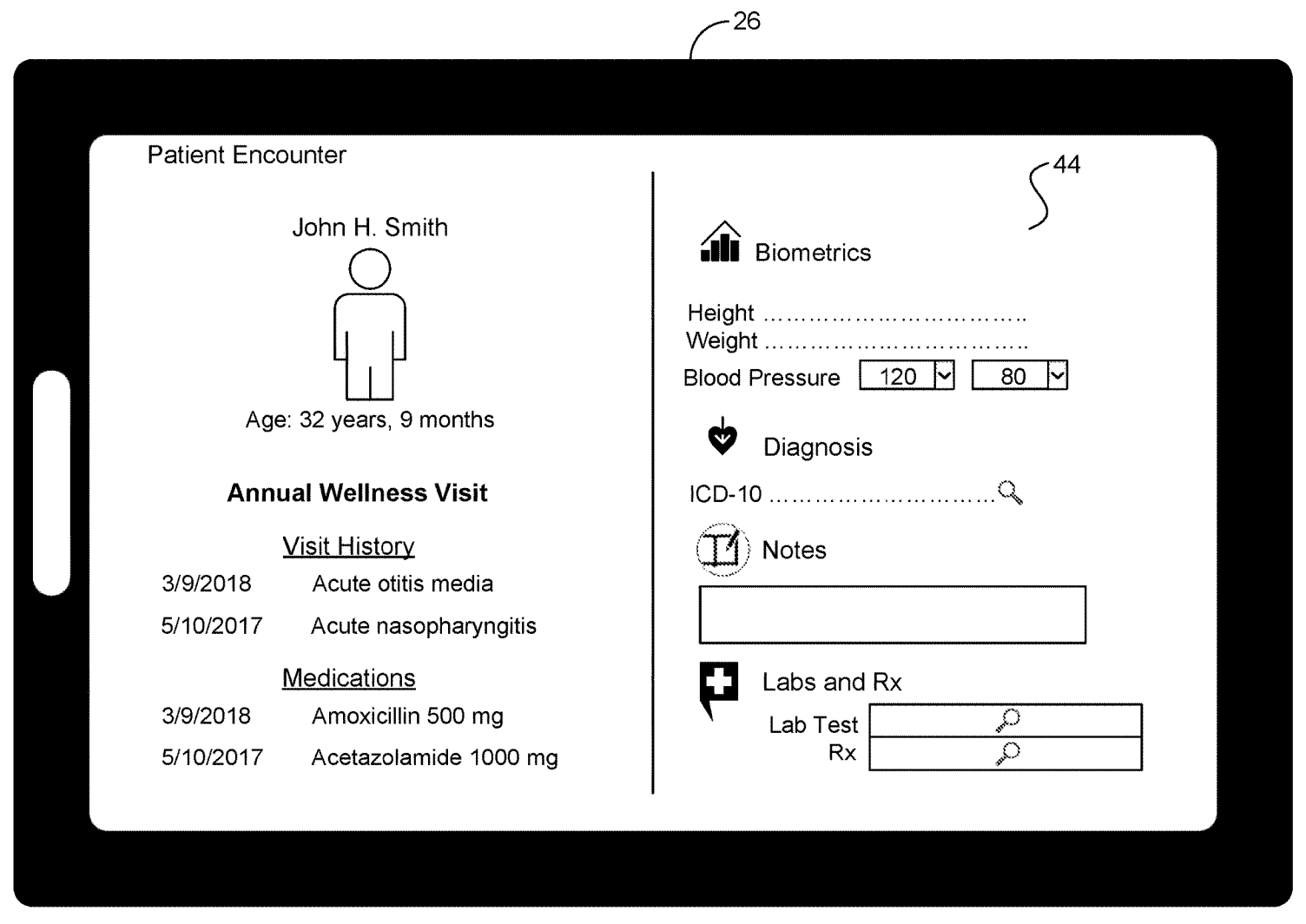
Figure 10:
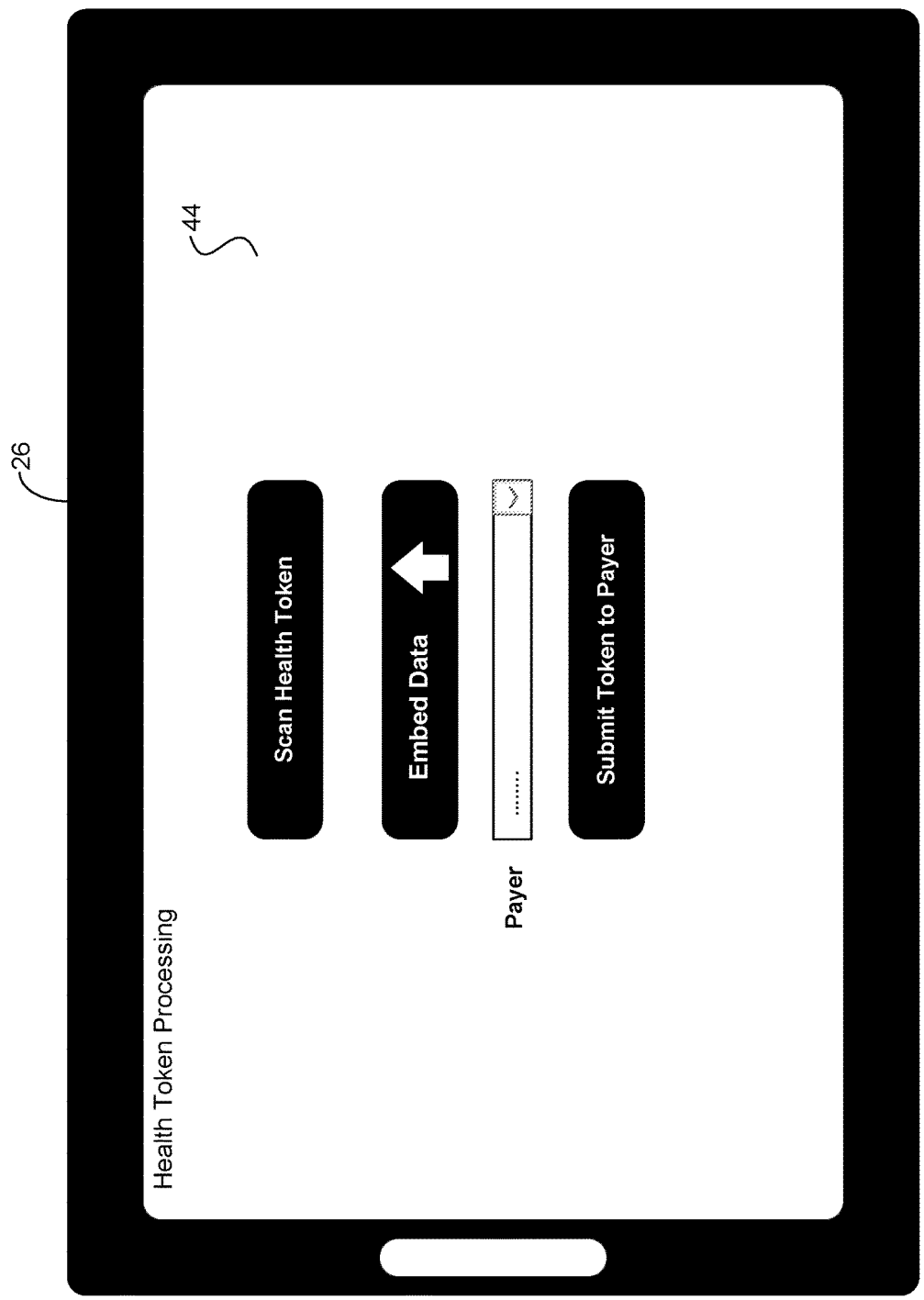
FIG. 10 is another exemplary display interface of the provider computer device, according to one embodiment.

FIG. 9 shows exemplary clinical encounter data as viewed at the display interface 44 of the provider computer display 26. An exemplary display interface 44 of the provider computer device 26 when using the health token application is shown in FIG. 10. As shown, the health token application may allow the healthcare provider 14 to scan the health tokens 22, embed clinical encounter data and other data into scanned health tokens 22, and submit health tokens 22 to a selected payer 16 in the health token system 10.

Figure 11:
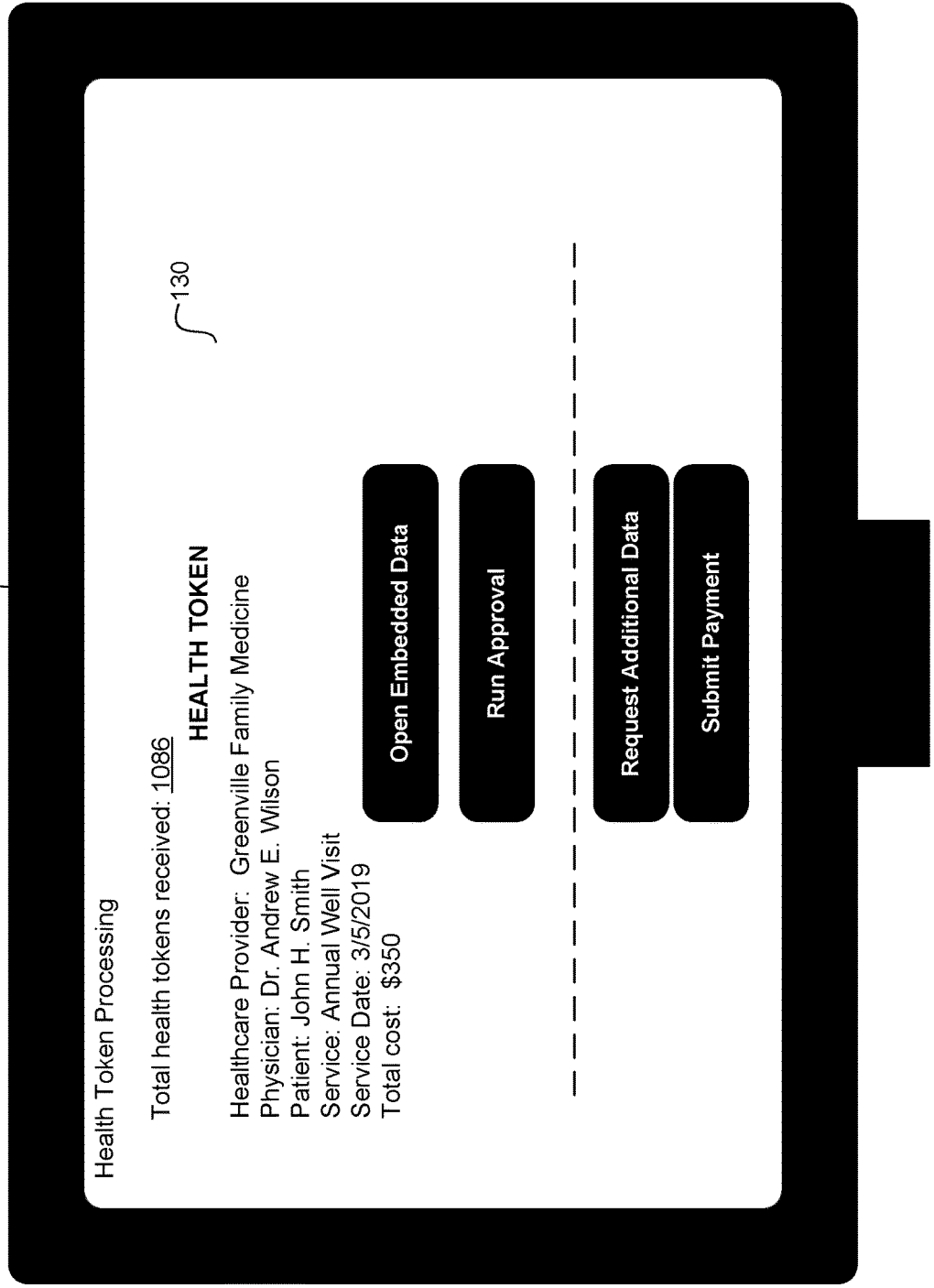
FIG. 11 is an exemplary display interface of the payer computer device, according to one embodiment.

An exemplary display interface 130 of the payer computer device 24 when using the health token application is shown in FIG. 11. The health token application may allow the payer 16 to view the health token 22 submitted by the healthcare provider 14, open and view any data embedded in the health token 22, run an approval algorithm to determine if the data embedded in the health token 22 satisfies the approval rules embedded in the health token 22, and request additional data from the health care provider 14 if the rules are not satisfied. Furthermore, the health token application may allow the payer 16 to electronically submit the full payment to the health care provider 14 if the approval rules are satisfied. It will be understood that the display interfaces of FIGS. 7-11 are merely exemplary and may include more or less features, and/or may have a different appearance in practice.

The present disclosure provides a solution to the need for more efficient revenue flow to healthcare providers for healthcare services, and for reducing healthcare provider overhead costs associated with payment collection. The health token system implements blockchain technology to support healthcare service payments and data sharing. The health token system results in more timely healthcare provider revenue flow, as post-service claim adjudication is eliminated, and service pricing and patient cost share is established prior to the healthcare service being performed. As the patient fulfills his or her cost share obligations prior to visiting the healthcare provider, patient debt and associated provider overhead costs for patient debt collection may be eliminated. The health token system may also allow for the negotiation of better healthcare service costs due to the elimination of unpaid patient debt and the faster revenue cycle. Additionally, the health token facilitates the flow of data between the healthcare provider and the payer, which may improve the timeliness of payer approval and provide better adherence to published healthcare guidelines. The healthcare payer may use the clinical encounter data to avoid future, unnecessary procedures, and to respond to any adverse situations that could negatively impact the patient's current and future health outcomes. Even further, the system provides a common digital healthcare platform that is shared by patients, healthcare providers, and healthcare payers, and improves financial predictability for healthcare services for all parties. The platform may improve patients' healthcare experience through simplification, by improving the transparency of healthcare costs, and by aligning with modern digital shopping experiences.

What is claimed is:

1. A computer-implemented method for expediting processing of a payment for a patient's healthcare service with a healthcare provider, comprising:
   prior to the healthcare service being rendered, displaying an exact out-of-pocket cost for the patient for the healthcare service at a display interface associated with a computer device of the patient;
   issuing the patient a health token as cryptocurrency for future payment of the healthcare service, the health token being stored in a digital wallet on the computer device of the patient;
   receiving the health token from the healthcare provider after the healthcare provider: 1) renders the healthcare service, 2) receives the health token from the patient for payment of the healthcare service, and 3) embeds data pertaining to the healthcare service into the health token, the data including clinical encounter data for the healthcare service and approval rules for an approval of the healthcare service;
   determining, based on the received health token, that the clinical encounter data for the healthcare service meets the approval rules;
   generating the approval of the healthcare service,
   and issuing a full payment to the healthcare provider for the healthcare service based on the determining step.

2. The computer-implemented method of claim 1, further comprising collecting from the patient a payment including the out-of-pocket cost for the healthcare service prior to issuing the health token to the patient.

3. The computer-implemented method of claim 1, wherein issuing the patient the health token comprises activating the health token if the patient does not have an out-of-pocket cost for the healthcare service.

4. The computer-implemented method of claim 1, wherein the method is at least partially performed using a payer computer device associated with a payer for the healthcare service.

5. The computer-implemented method of claim 4, wherein the payer is a healthcare insurer with which the patient has a healthcare plan.

6. The computer-implemented method of claim 5, further comprising providing a computer-downloadable health token application to the healthcare provider that allows the healthcare provider to scan the health token stored in the patient's digital wallet after rendering the healthcare service, embed the data into the health token, and to submit the health token to the payer for redemption at a provider computer device.

7. The computer-implemented method of claim 6, further comprising using the health token application at the payer computer device to view the health token received from the healthcare provider, view the data embedded on the health token, and determine if the data embedded in the health token satisfies the approval rules.

8. The computer-implemented method of claim 7, further comprising providing the patient with the computer-downloadable health token application to allow the patient to view the out-of-pocket cost for the healthcare service, select the healthcare service, pay any out-of-pocket cost for the healthcare service, and obtain the health token for payment of the healthcare service at the patient's computer device.

9. A health token system for expediting processing of a payment for a patient's healthcare service with a healthcare provider, comprising:
   a blockchain network including at least a payer computer device associated with a payer, a provider computer device associated with the healthcare provider, and a patient computer device associated with the patient;
   a patient interface module associated with the payer computer device configured to issue the patient a health token as cryptocurrency for payment of the healthcare service prior to the healthcare service being rendered, the health token being stored in a digital wallet on the patient's computer device;
   a provider interface module associated with the payer computer device configured to receive the health token from the provider computer device after the healthcare provider renders the healthcare service and receives the health token from the patient for payment of the healthcare service, the health token including clinical encounter data for the healthcare service and approval rules for an approval of the healthcare service; and an approval module associated with the payer computer device configured to determine, based on the health token received by the provider interface, that the clinical encounter data for the healthcare service meets the approval rules, generate an approval of the healthcare service in response to the clinical encounter data of the health token received by the provider interface meeting the approval rules, and to-approve issuance of a full payment to the healthcare provider for the healthcare service in response to the determination based on the health token received by the provider interface.

10. The health token system of claim 9, wherein the health token is generated and validated using blockchain technology.

11. The health token system of claim 9, wherein the payer computer device is associated with a healthcare insurer with which the patient has a healthcare plan.

12. The health token system of claim 9, wherein the provider interface module is configured to submit a request for additional data to the provider computer device if the healthcare service is not approved.

13. The health token system of claim 9, wherein the patient's computer device includes a health token application downloaded thereon that allows the patient to view an out-of-pocket cost for the healthcare service, select the healthcare service, pay any out-of-pocket cost for the healthcare service, and obtain the health token for payment of the healthcare service at a display interface.

14. The health token system of claim 13, wherein the patient interface module is configured to issue the health token to the patient after collecting a payment from the patient that includes the patient's out-of-pocket cost for the healthcare service.

15. The health token system of claim 13, wherein the provider computer device includes the health token application downloaded thereon, the health token application allowing the healthcare provider to scan the health token stored in the patient's digital wallet, embed data pertaining to the healthcare service into the health token, and submit the health token to the payer computer device for redemption.

16. The health token system of claim 15, wherein the approval module is configured to approve the healthcare service based at least on the data embedded in the health token.

17. A computer-implemented method for expediting processing of a payment for a patient's healthcare service with a healthcare provider, comprising:

providing the patient with a list of healthcare services at a display interface of a computer device of the patient;

presenting the patient with an exact out-of-pocket cost for each of the healthcare services at the display interface;

allowing the patient to select a desired healthcare service from the list;

collecting from the patient a payment corresponding to the out-of-pocket cost for the selected healthcare service if the selected healthcare service includes an out-of-pocket cost;

prior to the healthcare service being rendered, issuing the patient a health token for future payment of the healthcare service, the health token being generated using blockchain technology and being stored in the patient's computer device;

receiving the health token from the healthcare provider after the healthcare provider renders the healthcare service, receives the health token from the patient for payment of the healthcare service, and embeds data pertaining to the healthcare service into the health token, the data including clinical encounter data for the healthcare service and approval rules for an approval of the healthcare service;

determining, based on the received health token, that the clinical encounter data for the healthcare service meets the approval rules;

generating the approval of the healthcare service, and providing a full payment to the healthcare provider for the healthcare service based on the determining step.

* * * * *